(12) United States Patent
Kishida et al.

(10) Patent No.: US 7,468,263 B2
(45) Date of Patent: Dec. 23, 2008

(54) METHOD FOR CONTROLLING BIOLOGICAL FUNCTION WITH MECHANICAL VIBRATION AND DEVICE THEREFOR

(75) Inventors: Akio Kishida, Toyonaki (JP); Tsutomu Furuzono, Suita (JP); Kozo Miyazaki, Minoo (JP); Toru Masuzawa, Hitachi (JP)

(73) Assignee: Miwatec Co., Ltd., Inagi-shi (JP)

( * ) Notice: Subject to any disclaimer, the term of this patent is extended or adjusted under 35 U.S.C. 154(b) by 333 days.

(21) Appl. No.: 11/069,863

(22) Filed: Feb. 28, 2005

(65) Prior Publication Data
US 2005/0153437 A1    Jul. 14, 2005

(51) Int. Cl.
*C12N 13/00* (2006.01)
*C12M 3/00* (2006.01)
(52) U.S. Cl. .............. 435/173.8; 435/173.1; 435/289.1
(58) Field of Classification Search ........... 435/173, 435/173.1, 173.8, 289.1
See application file for complete search history.

(56) References Cited

U.S. PATENT DOCUMENTS

| | | | |
|---|---|---|---|
| 5,821,116 A * | 10/1998 | Herman | 435/285.1 |
| 6,156,549 A * | 12/2000 | Drewes et al. | 435/173.7 |
| 6,645,162 B2 * | 11/2003 | Friedman et al. | 601/2 |
| 6,652,473 B2 * | 11/2003 | Kaufman et al. | 601/1 |
| 7,165,451 B1 * | 1/2007 | Brooks et al. | 73/579 |
| 2002/0077550 A1 * | 6/2002 | Rabiner et al. | 600/439 |
| 2002/0146817 A1 * | 10/2002 | Cannon et al. | 435/289.1 |
| 2003/0163056 A1 * | 8/2003 | Osypka et al. | 600/504 |
| 2003/0163068 A1 * | 8/2003 | Kang | 601/15 |

FOREIGN PATENT DOCUMENTS

| | | |
|---|---|---|
| JP | 11004896 | 1/1999 |
| JP | 11169167 | 6/1999 |
| JP | 11196857 | 7/1999 |
| WO | 00/78932 | 12/2000 |

* cited by examiner

*Primary Examiner*—Herbert J Lilling
(74) *Attorney, Agent, or Firm*—Lipsitz & McAllister, LLC

(57) ABSTRACT

Methods and apparatus for controlling biological functions with mechanical vibration are provided. Stimulation is applied to cells of one of an organism, bacteria or virus by mechanical vibration. The biological function comprises biological functions relating to cell growth. The biological functions relating to cell growth may include at least one of cell cultivation, cell proliferation, cell fusion, and cell differentiation.

9 Claims, 5 Drawing Sheets

(B) vibration(100 Hz) was loaded (after one hour). (40 times magnification)

(A) No vibration was loaded. (after one hour)

METHOD FOR CONTROLLING BIOLOGICAL FUNCTION WITH MECHANICAL VIBRATION AND DEVICE THEREFOR

BACKGROUND OF THE INVENTION

1. Field of the Invention

The present invention relates to a method for controlling biological functions with mechanical vibration and the device therefor. More particularly, the invention relates to a method for controlling biological functions through the application of mechanical vibration, thus making it possible to artificially control the functions of cells, tissues and the like, and a device therefor.

2. Detailed Description of the Prior Art

Methods for controlling the cellular functions of cultivated cells as biological material have been extensively researched and evaluated, most of which additionally involved liquid factors such as proteins. Methods for transducing genes or adding polymer materials have been also reported upon. However, in methods accompanied by the addition of xenobiotica, the origin of the liquid factors to be added may cause problems in many cases. For example, when an animal-derived liquid factor exists, the type of the animal from which the liquid factor was derived, namely, whether the liquid factor is from a rabbit, sheep, human being, or other may cause problems. Further, there are many cases in which the cost of the liquid factors is a problem. Regarding gene transduction, various methods are under examination, namely, electroporation, a method for transducing genes by using a virus as a vector, a method for promoting gene transduction by using synthetic substances or the like, or a method for directly transducing genes by using micro syringe. However none of the foregoing has so far provided satisfactory effects. In addition, a method for using viruses is very effective at the investigation level, but when the method is applied to the human body as a therapeutic method, problems of an etiologic nature, safety, etc. always develop.

In relation to physical methods, controlling cellular functions by using methods such as hydrostatic pressure, cell spreading, and ultrasonic wave are also considered. It is known that stimulation by these physical methods effectively contributes to growth that includes the proliferation and differentiation of cells and tissues through the activation of various biological factors such as interleukin, cytokine and TNF-α or through the regulation of mechanisms such as inhibition and secretion.

However, with respect to the conventional methods for applying physical stimulation, the correlation between stimulation and the effect on cells is not always clear, and guidelines for selecting the method of applying the stimulation or controlling conditions of applying the stimulation are not presented. Thus, the methods for applying physical stimulation are not established as a simple and effective way which is practical.

In light of the situation described above, the present invention has the objective of providing a new method for controlling various biological functions and the appropriate device which solves conventional technology problems. The present invention avoids using conventional liquid factors that have origin-related problems or using synthetic polymer materials. Alternatively, the present invention may reduce to a large extent the quantity of such liquid factors or synthetic polymers required. The present invention also takes advantage of the characteristics of applying stimulation as a physical method to promote the proliferation of cells and reactions within cells or tissues simply, effectively and in a practical way, thereby inducing differentiation. In addition, the present invention also provides a new method for transducing genes.

SUMMARY OF THE INVENTION

In solving the foregoing problems, the first objective of the invention is to provide a method for controlling biological functions with mechanical vibration, whereby tissues or cells of organisms, bacteria and viruses are stimulated by mechanical vibration.

The second objective of the invention is to provide a method for controlling biological functions wherein stimulation is applied by temporary, continuous or intermittent mechanical vibration. The third objective of the invention is to provide a method for controlling biological functions wherein stimulation is applied by mechanical vibration, the amplitude of which is 100 μm or lower. The fourth objective of the invention is to provide a method for controlling biological functions wherein stimulation is applied by mechanical vibrations, the frequency of which is 100 MHz or lower. And the fifth objective of the invention is to provide a method for controlling biological functions wherein stimulation is applied by mechanical vibration, the amplitude of which is 20 μm or lower and the frequency of which is in the range of 1 Hz to 10 MHz.

Furthermore, the sixth objective of the invention is to provide a cultivation method, wherein cells or tissues are cultivated. using the stimulation described in any one of above methods.

The seventh objective of the invention is to provide a method wherein cultivated cells are increased in initial adhesion ability. An eighth objective of the invention being to provide a method wherein the cultivated cells are promoted to proliferation.

The ninth objective of the invention is to provide a method wherein cell fusion is promoted. The tenth objective of the invention is to provide a method wherein xenobiotica can be introduced into cells. The eleventh objective of the invention is to provide a method wherein genes, proteins or drugs can be introduced as xenobiotica.

In addition, the twelfth objective of the invention is to provide a device for controlling biological functions through the application of mechanical vibrations to tissues or cells of an organism, bacteria or viruses, the device comprising a means for generating mechanical vibrations and also a means for transferring and applying vibration to give the generated mechanical vibration as stimulation. The thirteenth objective of the invention is to provide a device for controlling biological functions wherein the means for transferring and applying vibration has a solid substrate with which tissues, cells, bacteria or viruses come into contact.

DETAILED DESCRIPTION OF THE PREFERRED EMBODIMENT

Figure 1:
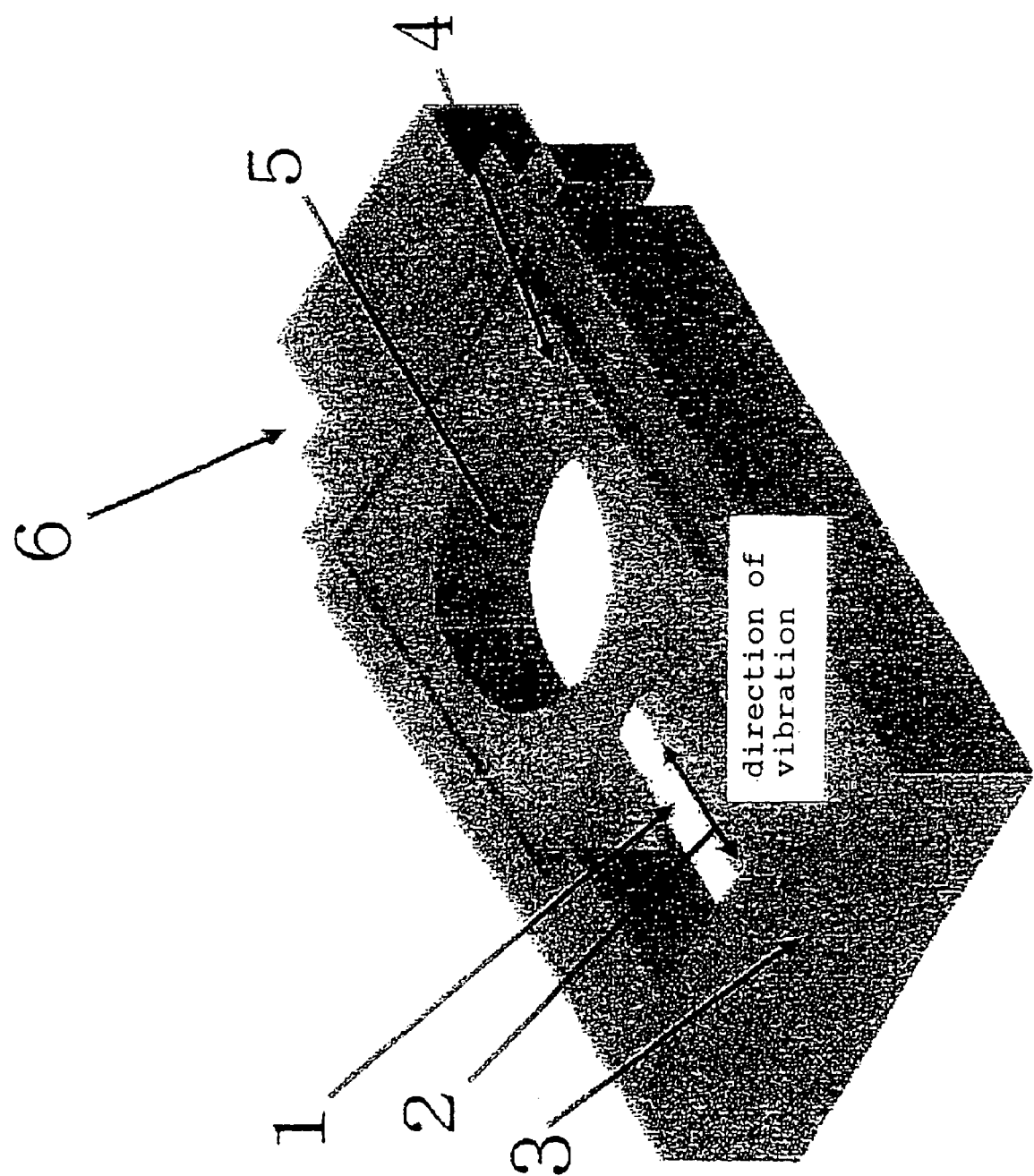
FIG. 1 is a perspective view schematically illustrating a device of the invention.

The invention has the above described characteristics, and will be explained in detail for the preferred embodiments, which are as follows.

The tissues and cells of the organisms, bacteria, and viruses to be the object of the present invention may be derived from any kind of organism, bacteria, or virus and be of any origin. For example, if the object is a cell, the cell may be a plant cell, insect cell, mammal cell, and various tissues constituted with such cells. Accordingly, a cell derived from a human, a mouse, a sheep, a rabbit, a monkey, or the like can be named as an example for the mammal cell. Further, the cell may be an adherent cell or a float cell.

The method for controlling biological functions according to the present invention which is to be applied to such various objects will find its actual application or practical object of its use in tissue culture, cell culture, fermentation, budding, growth and fruiting, weeding and preservation of plants, treatment of animals or humans, removal of bacteria, disinfections, inactivation of viruses and the like.

More specific functions to be controlled are mainly related to events that will take place inside cells, for example, adhesion, proliferation, differentiation, biosynthesis, migration, change in configuration, metabolism, apoptosis, genetic transformation, necrosis, inactivation, and budding of yeast. As for events that will take place by interaction of cells with an outer environment, cell fusion, transudation of inheritance, protein or drugs, and destruction of cells are named as examples.

Stimulation with mechanical vibration has to date not been reported in connection with the above-described method for controlling biological functions, which is epoch-making in terms of a wide scope of applications, applicability to a diversity of objects, as well as remarkable effects and actions.

In the present invention in which vibration is applied to cells, tissues and others to control biological functions, the "mechanical vibration" referred to is in general considered to be 100 μm or smaller in amplitude. Amplitude is preferably 20 μm or lower in view of cell size on float, however, when consideration is given to fibroblastic cells which elongate up to about 100 μm, the practical amplitude is up to 100 μm. Further, since the amplitude is related to the magnitude of frequency, it is preferable to select the amplitude and the frequency so that target tissues, cells and others will not be physically crushed.

Frequency is restricted in its selection in view of the above fact, and, in general, a frequency of 100 MHz or lower is practical and preferable.

It is preferable that amplitude is 20 μm or lower and frequency is in the range from 1 Hz to 10 MHz in the case of cells. In general, preferable frequency is from 10 Hz to 1 MHz, depending on types and origins of cells and tissues to be cultivated.

Actual effect on cells is little when the frequency is less than 1 Hz, while the possibility of damage to cells and tissues must be considered when the frequency exceeds 10 MHz.

When vibration is applied to cells and tissue, it is preferable to use a different wave form with consideration given to cell structure, cell membrane and membrane protein of the cells or tissues as targets of the vibration as well as to the biological functions and roles of bacteria and viruses. Further, as described above, the vibration may be continuous or intermittent, and may be given by non-stationary waves such as a pulse wave in addition to a stationary wave.

The "mechanical vibration" of the present invention is essentially different in the effect from the vibration caused by ultrasonic irradiation (which is a longitudinal wave constituted with dilatational wave) in which a medium causes vibration. In the present invention, a solid substrate vibrates while in contact with tissues, cells, bacteria or viruses. In this instance it is possible to distinguish horizontal movement from longitudinal movement as indicated by the different direction of vibration.

The cells, tissues or the like may take various forms when they are vibrated. Namely, they may be placed on a supporting solid substrate in a flat form, be in a form of a three-dimensional mass, or be in a form of fine particles. Further, they may coexist with liquid. The mechanical vibration is effective both in and out of the living body.

The device claimed in the invention is provided with a "means to generate vibration" and a "means to transfer and apply vibration", which are not to be particularly restricted to their constitutions. For example, as illustrated in FIG. 1, a device for cell cultivation of which a laboratory dish plate (4) slidably attached on a base (3) is vibrated by a piezoelectric element (1) to give vibration to a laboratory dish on a laboratory dish setting part (5) is considered as a typical example of the device according to the present invention. The device illustrated in FIG. 1 is also provided with a over-current detection sensor (6). The piezoelectric element (1) is to produce vibration in the direction shown by an arrow (2).

The device of the present invention may be constituted in accordance with types and properties of the target tissues, cells, viruses and soon, as well as the biological functions to be controlled. In addition to the device producing horizontal vibration as illustrated in FIG. 1, a device producing longitudinal vibration by arraying vibration elements in a longitudinal direction, a device producing vibration by using an external magnetic field, and an array-type vibration device by arranging transducers with a pattern, or the like are contemplated by the present invention. Various types of a solid substrate in contact with tissues, cells, bacteria, or viruses may be considered as the means to transfer and apply vibration. The "substrate" may not be in a flat plate form. The plate may be in various forms such as a curved surface, a foreign shape, particles, a fiber, or the like. The substrate may also be available in a soft solid such as viscous substance, jelly, gel, sponge and rubber, and the like, in addition to a hard solid.

The present invention described above provides a new method for applying stimulation and a device therefor, which can control biological functions of cells and tissues. The method and the device does not use liquid factors or synthetic polymer materials having the problem related their origin as seen in the conventional art, or can drastically reduce the amount of usage of the factors or polymers. With the characteristics of applying stimulation as the physical method, adhesion, proliferation of cells and reaction in cells or tissues are promoted to induce differentiation in a more practical, simple and effective manner; moreover, the introduction of xenobiotica such as new genes is facilitated.

The invention will be explained in more detail by referring to the following example embodiments, which should be construed so as not to restrict the present invention.

EMBODIMENT

As a "device for controlling biological functions", a device constituted as shown in FIG. 1 (discussed above) which has displacement range from 0 to 15 μm, an operational frequency from 1 Hz to 10 kHz, a built-in sensor for strain gauge position, and a strain gauge resolution of 1 nm. Further, the object to be vibrated is a laboratory dish having a diameter of 50 mm.

Figure 2:
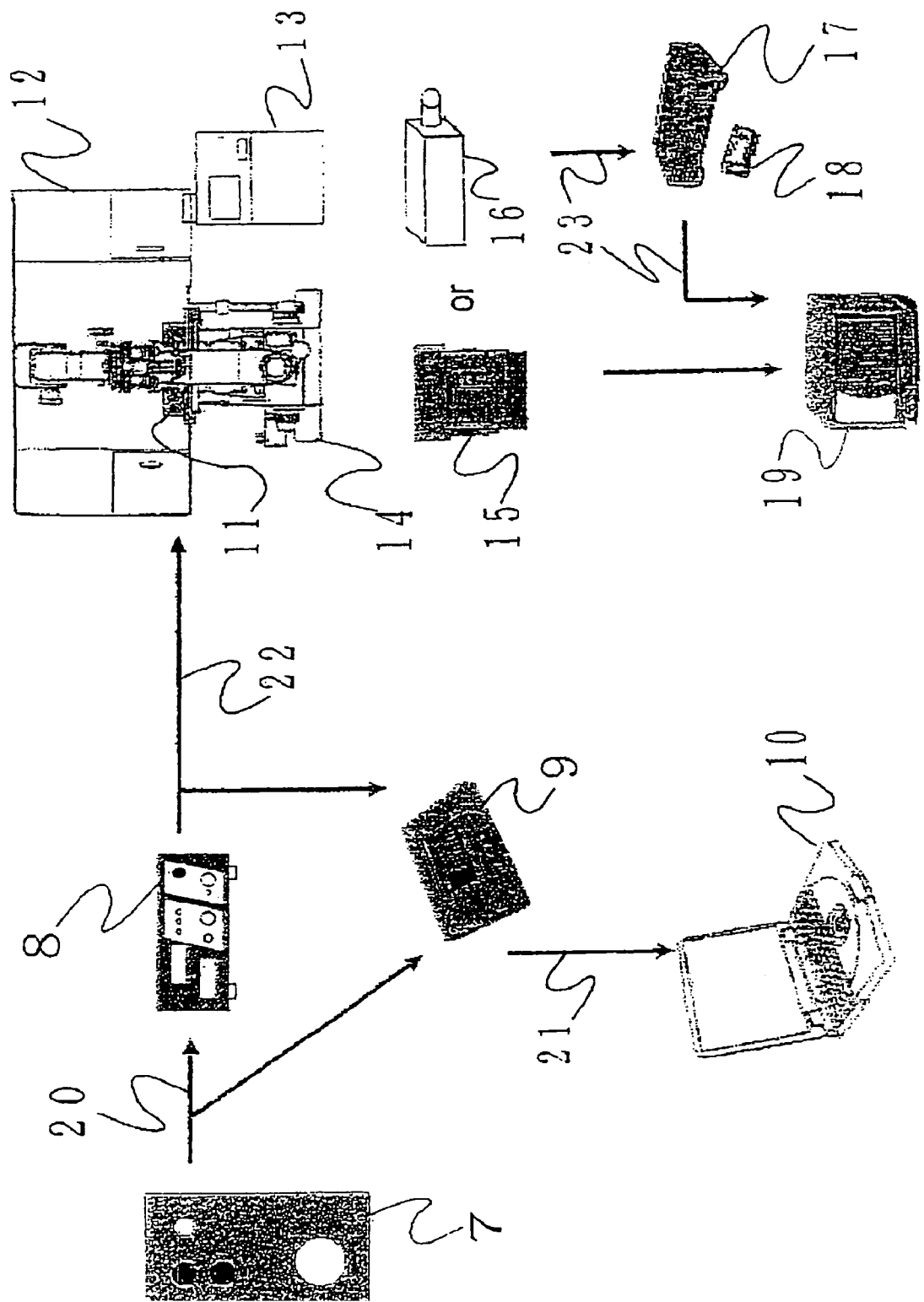
FIG. 2 is a block diagram illustrating an example embodiment of an experimental system in accordance with the present invention.

FIG. 2 shows schematically a block diagram of an experimental system in which a vibration device is used.

A vibration load device (11) is installed in an ambient air blocking box (12) and is temperature controllable by a temperature adjusting device (13). Cultivation states can be observed by a microscope (14), and the source of the observation is photographed by a digital camera (15) or a CCD camera (16). The photographed image can be recorded as analogue signals by a cell-change recording device (17) or a recording medium (18) and/or can be directly monitored by a confirmation monitor (19).

The device-driving voltage signal (22) of the vibration device (11) is transmitted by a function generator (7) and a driver (8). The signal (22) can be recorded and monitored, for example, by an oscilloscope (9) and a notebook computer (10).

Embodiment 1

Action on Initial Adhesion

In an embodiment 1, effects on initial adhesion of cultivated cells obtained by ordinary cultivation with no vibration applied and cultivation with vibration applied were compared and examined. The results were shown in FIG. 3 and FIG. 4.

Figure 3:
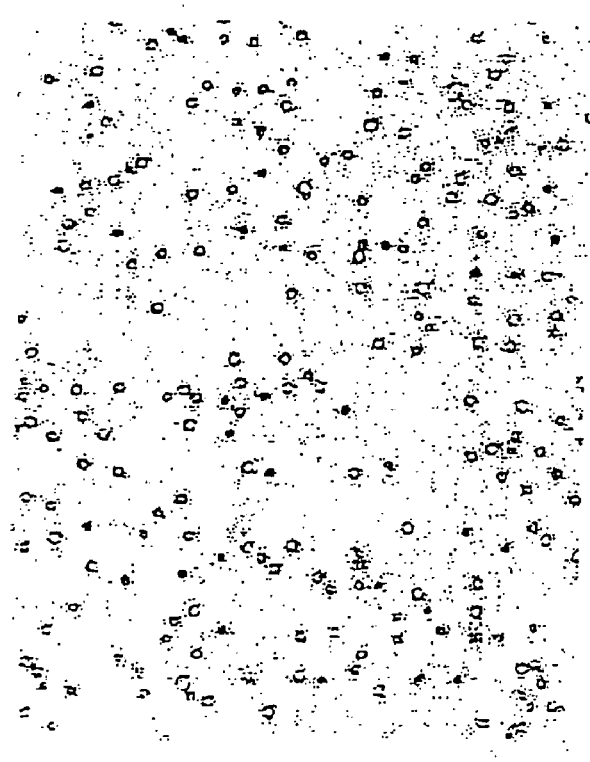
FIG. 3 shows microscopic images of the result of embodiment 1. The image (A) shows the case where no vibration was loaded, and the image (B) shows the case where vibration was loaded.

In FIG. 3, the instrumentation of the initial adhesion ability of the cultivated cells with vibration load is shown as an observed image by a microscope. Mouse-derived fibroblastics (L929 cells) were used as cultivated cells. The L929 cells were prepared for cultivation without vibration and for cultivation with vibration, and seeded respectively on a laboratory dish having diameters of 6 cm for cultivation. On seeding, vibration was applied for one hour at a frequency of 100 Hz and amplitude of 9 μm. After one hour, the L929 cell (A) to which no vibration was loaded exhibited a spherical shape and did not adhered to the surface of the laboratory dish. In contrast, the L929 cell (B) to which vibration was loaded underwent cell activation, already adhered to the surface of the laboratory dish, and exhibited signs of starting differentiation, which were about 4 times greater than the conventional initial adhesion capacity.

Figure 4:
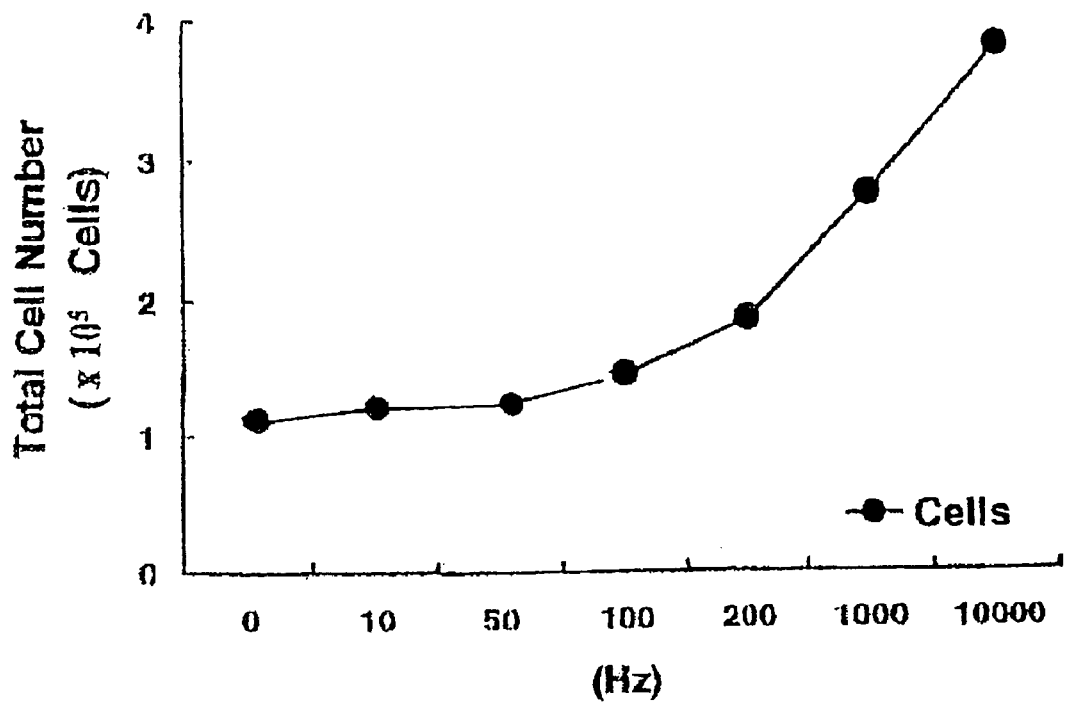
FIG. 4 is a drawing illustrating a profile of cell measurement at embodiment 1.

Next, the cell number was counted by using human umbilical vein endothelial cells used for artificial blood vessels and others. A laboratory dish of $5 \times 10^5$ cells/6 cm-diameter for the initial cell number was prepared and seeded respectively. One hour after seeding of the cells, vibration was loaded and cultivation was conducted for one hour. Vibration was applied at a frequency from 0 to 10000 Hz and at an amplitude from 0 to 15 μm, and the cells which are adhered to the surface of laboratory dishes under the respective vibration conditions were counted. As the result, it was confirmed that at amplitude of 5 μm, as shown in FIG. 4, 20% of the cultivated cells were adhered to the surface of the laboratory dish when no vibration was loaded, whereas they were adhered at a higher percentage, namely, about 80%, when vibration was loaded.

Embodiment 2

Action on Proliferation of Cultivated Cells

Action of vibration on proliferation of cultivated cells was examined. The result of the examination is shown in FIG. 5.

Human umbilical vein endothelial cells were prepared and seeded on laboratory dishes for cultivation. Eighteen hours after seedling, vibration was loaded for one hour, and cultivated for another 48 hours to count the cell number. Vibration was applied at frequency of 0, 10, 100, 1000, and 10000 Hz, and in amplitude of 5 μm. Cultivation was conducted at the initial cell number of a laboratory dish of $0.5 \times 10^5$ cell/6 cm-diameter.

Figure 5:
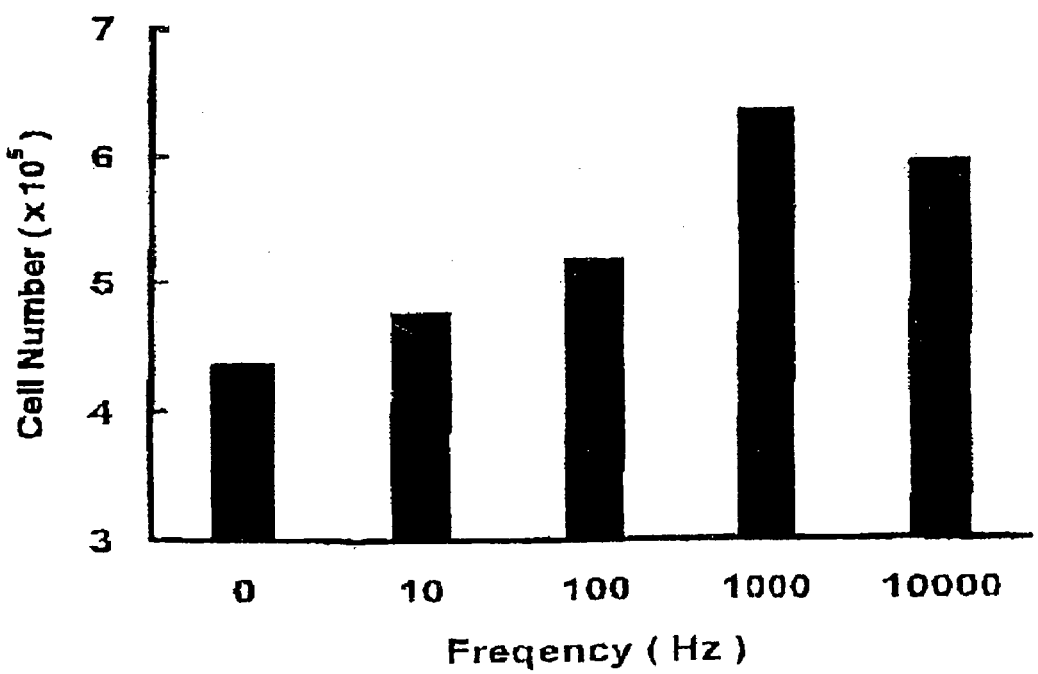
FIG. 5 is a drawing illustrating the effect on cell proliferation as the result of embodiment 2.

As shown in FIG. 5, a remarkably greater proliferation was found when vibration was loaded than when no vibration was loaded.

Embodiment 3

Effect on Cell Fusion

Effect of vibration on cell fusion was examined.

Figure 6:
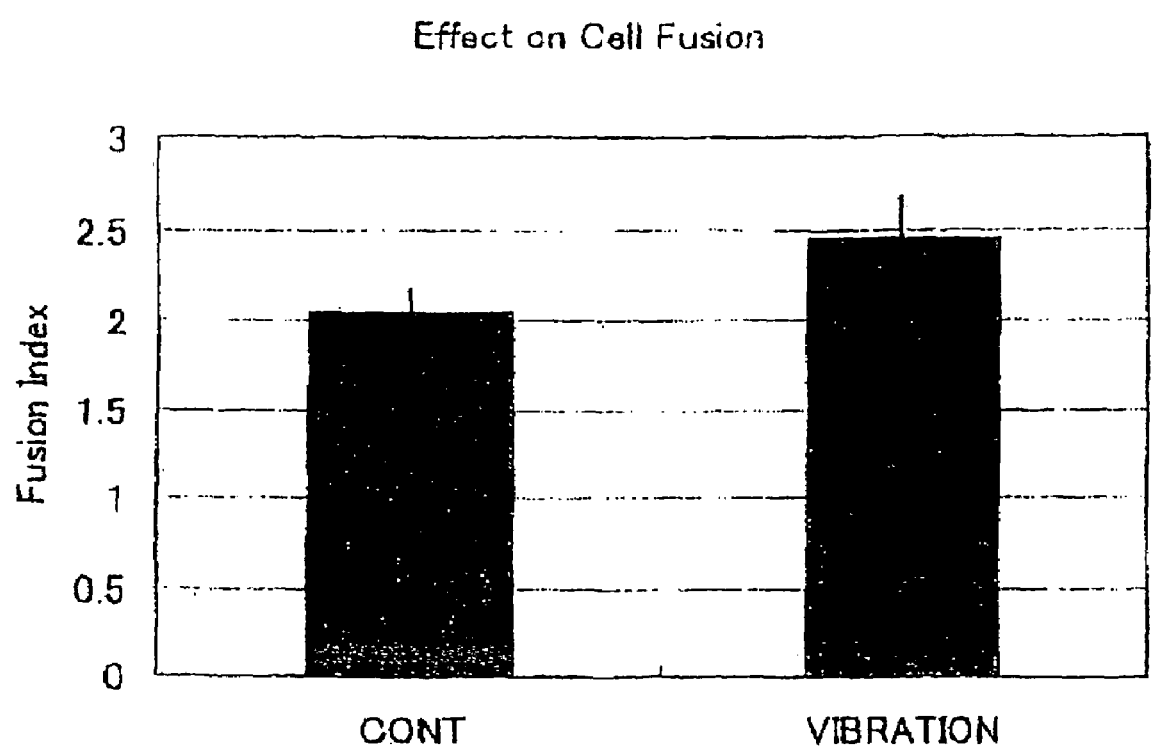
FIG. 6 is a drawing illustrating the effect cell fusion in embodiment 3.

The above-described L929 cells are used and a laboratory dish of $5 \times 10^5$ cells/6 cm-diameter for initial cell number is prepared. Vibration was loaded at a frequency of 500 Hz and an amplitude of 5 μm for one hour. After vibration was loaded, cultivation was conducted for 48 hours and the cell number was counted, the result of which is shown in FIG. 6. "Fusion index" described in FIG. 6 represents the mean number of multinucleated cells which were microscopically observed at 20 fields under magnification of 40 times on the 6 cm-diameter dish.

In the first place, the L929 cells were densely seeded to form multinucleated cells. An average number of multinucleated cells were two when no vibration of control (CONT) was loaded. On the other hand, the average number of multinucleated cells were 2.5 and the number of multinucleated cells formed at the center of the dishes were 4 when vibration was loaded. This result indicates about a 2-times greater cell fusion index at the center. Further, a difference between the cells to which no vibration was loaded and those to which vibration was loaded was clearly discriminated even microscopically.

Embodiment 4

Transduction of Genes into Cells

Evaluation was made for introduction of extraneous genes by vibration.

Human umbilical vein endothelial cells were used as cultivated cells. As extraneous genes, cells of pCMV-GFP (21 μg/mL) having green fluorescence-generating ability were used. In the first place, the cells were seeded at $4 \times 10^5$ on 6 cm-diameter laboratory dishes, allowed to stand for one day, and changed culture one hour before vibration was applied. One hour later, plasmid DNA containing GFP genes were added to the culture so as to give 2 μg/mL, subjected to 30 minute-incubation and then given vibration, as was done in embodiment 2. 48 hours later, a cytometer was used to count all viable cells under a phase contrast microscope. Further, the same samples were used to count green-light emitting cells under a fluorescent microscope. Vibration was loaded at a frequency of 100, 1000 and 10000 Hz, in amplitude of 51μ for one hour A control to which no vibration was applied was also prepared. Accordingly, the moderate fluorescence degree of one to two was indicated in vibration frequency of 100 Hz and 10000 Hz and the intense fluorescence degree of three was presented in vibration frequency of 1000 Hz while the fluorescence degree was 0 in the control group. This finding confirmed that the stimulation by vibration was great particularly in the frequency of 1000 Hz and extraneous genes were effectively introduced.

ADVANTAGEOUS EFFECT OF THE INVENTION

As explained so far in detail, the present invention makes it possible to artificially control biological functions of cells, tissues and the like by applying mechanical vibration to stimulate biological samples such as cells and tissues.

The invention also provides a new method for introducing extraneous genes by activating cultivated cells and promoting proliferation.

The present invention provides an epoch-making technology in various fields such as pathological diagnosis, gene therapy, regenerative medicine, reproductive medicine, safety assessment, minimally invasive surgery, gene analysis, and biogenic simulator.

REFERENCES 1 piezoelectric element (transducer)
2 direction of vibration
3 base
4 laboratory dish plate
5 laboratory dish setting part
6 over-current detection sensor
7 function generator
8 driver
9 oscilloscope
10 notebook computer
11 vibration load device
12 ambient air blocking box
13 temperature adjusting device
14 microscope
15 digital camera
16 CCD camera
17 cell-change picture recording device
18 recording medium
19 confirmation monitor
20 input voltage signal
21 data on wave form
22 device-driving voltage signal
23 analogue signal

What is claimed is:

1. A method for controlling biological functions with mechanical vibration, comprising:
    applying stimulation to cells of one of an organism, bacteria or virus by mechanical vibration, said mechanical vibration comprising at least one of a horizontal movement and a longitudinal movement;
    wherein said biological functions comprise biological functions relating to cell growth, said biological functions relating to cell growth comprising at least one of cell cultivation, cell proliferation, cell fusion, and cell differentiation.

2. The method for controlling biological functions according to claim 1, wherein the stimulation is applied by one of temporary, continuous or intermittent mechanical vibration.

3. The method of controlling biological functions according to claim 1, wherein the stimulation is applied by the mechanical vibration, amplitude of which is 100 μm or lower.

4. The method for controlling biological functions according to claim 1, wherein the stimulation is applied by the mechanical vibration, frequency of which is 100 MHz or lower.

5. The method for controlling biological functions according to claim 4, wherein the stimulation is applied by the mechanical vibration, amplitude of which is 20 μm or lower and frequency of which is in the range from 1 Hz to 10 MHz.

6. The method for controlling biological functions according to claim 1, wherein said functions relating to cell growth comprise more than one of cell cultivation, cell proliferation, cell fusion, and cell differentiation.

7. The method for controlling biological functions according to claim 1, wherein the mechanical vibration is generated by a piezoelectric element.

8. The method for controlling biological functions according to claim 1, wherein the mechanical vibration is generated by a vibration load device situated within an airtight chamber.

9. The method for controlling biological functions according to claim 1, wherein the mechanical vibration is generated by one of: (a) a plurality of vibration elements arranged in a longitudinal direction; (b) an external magnetic field; and (c) an array of transducers.

* * * * *